United States Patent
Tirtowidjojo et al.

(10) Patent No.: US 9,403,741 B2
(45) Date of Patent: Aug. 2, 2016

(54) PROCESS FOR THE PRODUCTION OF CHLORINATED ALKANES

(71) Applicant: BLUE CUBE IP LLC, Midland, MI (US)

(72) Inventors: Max M. Tirtowidjojo, Lake Jackson, TX (US); David S. Laitar, Midland, MI (US); Matthew L. Grandbois, Midland, MI (US); William J. Kruper, Jr., Sanford, MI (US); Edward M. Calverley, Midland, MI (US)

(73) Assignee: BLUE CUBE IP LLC, Midland, MI (US)

( * ) Notice: Subject to any disclaimer, the term of this patent is extended or adjusted under 35 U.S.C. 154(b) by 0 days.

(21) Appl. No.: 14/773,833

(22) PCT Filed: Mar. 7, 2014

(86) PCT No.: PCT/US2014/022164
§ 371 (c)(1),
(2) Date: Sep. 9, 2015

(87) PCT Pub. No.: WO2014/164368
PCT Pub. Date: Oct. 9, 2014

(65) Prior Publication Data
US 2016/0023967 A1   Jan. 28, 2016

Related U.S. Application Data

(60) Provisional application No. 61/775,497, filed on Mar. 9, 2013.

(51) Int. Cl.
| | | |
|---|---|---|
| C07C 17/04 | (2006.01) | |
| C07C 17/10 | (2006.01) | |
| C07C 17/25 | (2006.01) | |
| C07C 17/06 | (2006.01) | |
| C07C 17/07 | (2006.01) | |

(52) U.S. Cl.
CPC ............... C07C 17/07 (2013.01); C07C 17/06 (2013.01); C07C 17/10 (2013.01); C07C 17/25 (2013.01); *Y02P 20/582* (2015.11)

(58) Field of Classification Search
CPC ........ C07C 17/04; C07C 17/10; C07C 17/25; C07C 17/06; Y02P 20/582
See application file for complete search history.

(56) References Cited

U.S. PATENT DOCUMENTS

| | | |
|---|---|---|
| 2,119,484 A | 5/1938 | Levine et al. |
| 2,179,378 A | 11/1939 | Metzger |
| 2,207,193 A | 7/1940 | Groll |
| 2,299,441 A | 10/1942 | Vaughan et al. |
| 2,302,228 A | 11/1942 | Kharasch et al. |
| 2,370,342 A | 2/1945 | Zellner |
| 2,378,859 A | 6/1945 | Martin |
| 2,435,983 A | 2/1948 | Schmerling |
| 2,449,286 A | 9/1948 | Fairbairn |
| 2,588,867 A | 3/1952 | Morris |
| 2,630,461 A | 3/1953 | Sachsse et al. |
| 2,688,592 A | 9/1954 | Skeeters |
| 2,762,611 A | 9/1956 | Monroe |
| 2,765,359 A | 10/1956 | Pichler et al. |
| 2,964,579 A | 12/1960 | Weller et al. |
| 2,973,393 A | 2/1961 | Monroe |
| 3,000,980 A | 9/1961 | Asadorian |
| 3,094,567 A | 6/1963 | Eaker |
| 3,112,988 A | 12/1963 | Coldren et al. |
| 3,444,263 A | 5/1969 | Fernald |
| 3,446,859 A | 5/1969 | Weil |
| 3,502,734 A | 3/1970 | Baird |
| 3,525,595 A | 8/1970 | Zirngibl et al. |
| 3,551,512 A | 12/1970 | Loeffler |
| 3,558,438 A | 1/1971 | Schoenbeck |
| 3,651,019 A | 3/1972 | Asscher |
| 3,676,508 A | 7/1972 | Krekeler |
| 3,819,731 A | 6/1974 | Pitt |
| 3,823,195 A | 7/1974 | Smith |
| 3,872,664 A | 3/1975 | Lohmann |
| 3,914,167 A | 10/1975 | Ivy |
| 3,920,757 A | 11/1975 | Watson |
| 3,926,758 A | 12/1975 | Smith |
| 3,948,858 A | 4/1976 | Weirsum |
| 3,954,410 A | 5/1976 | Pohl et al. |

(Continued)

FOREIGN PATENT DOCUMENTS

| | | |
|---|---|---|
| CH | 609022 | 6/1974 |
| CN | 101215220 | 7/2008 |
| CN | 101492341 | 7/2009 |
| CN | 101544535 | 9/2009 |
| CN | 101597209 | 12/2009 |
| CN | 101754941 | 6/2010 |
| CN | 101913979 | 12/2010 |
| CN | 101913980 | 12/2010 |
| CN | 101955414 | 1/2011 |
| CN | 101982227 | 3/2011 |

(Continued)

OTHER PUBLICATIONS

Bai, et al., "Isomerization of Tetrachloropropene to Promote Utilization Ratio of Triallate Raw Materials", Petrochemical Technology & Application, 2007, 25(1).

(Continued)

*Primary Examiner* — Shailendra Kumar
(74) *Attorney, Agent, or Firm* — Polsinelli PC

(57) ABSTRACT

Processes for the production of chlorinated alkanes are provided. The present processes comprise dehydrochlorinating one or more trichloroalkanes having from 3-6 carbon atoms and vicinal chlorine atoms, followed by a series of sequential chlorination and/or further dehydrochlorination steps. Because the trichloroalkane is first dehydrochlorinated, rather than being first chlorinated, greater specificity to desired tetra- and pentachloroalkanes can be seen.

11 Claims, 3 Drawing Sheets

(56) References Cited

U.S. PATENT DOCUMENTS

| | | |
|---|---|---|
| 4,038,372 A | 7/1977 | Colli |
| 4,046,656 A | 9/1977 | Davis et al. |
| 4,051,182 A | 9/1977 | Pitt |
| 4,319,062 A | 3/1982 | Boozalis et al. |
| 4,513,154 A | 4/1985 | Kurtz |
| 4,535,194 A | 8/1985 | Woodard |
| 4,614,572 A | 9/1986 | Holbrook |
| 4,644,907 A | 2/1987 | Hunter |
| 4,650,914 A | 3/1987 | Woodard |
| 4,661,648 A | 4/1987 | Franklin |
| 4,702,809 A | 10/1987 | Mueller |
| 4,714,792 A | 12/1987 | Muller et al. |
| 4,716,255 A | 12/1987 | Muller |
| 4,726,686 A | 2/1988 | Wolf |
| 4,727,181 A | 2/1988 | Kruper |
| 4,849,554 A | 7/1989 | Cresswell et al. |
| 4,894,205 A | 1/1990 | Westerman |
| 4,902,393 A | 2/1990 | Muller |
| 4,999,102 A | 3/1991 | Cox |
| 5,057,634 A | 10/1991 | Webster |
| 5,132,473 A | 7/1992 | Furutaka |
| 5,171,899 A | 12/1992 | Furutaka |
| 5,178,844 A | 1/1993 | Carter et al. |
| 5,246,903 A | 9/1993 | Harley |
| 5,254,771 A | 10/1993 | Cremer |
| 5,254,772 A | 10/1993 | Dukat |
| 5,254,788 A | 10/1993 | Gartside |
| 5,262,575 A | 11/1993 | Dianis |
| 5,315,044 A | 5/1994 | Furutaka |
| 5,367,105 A | 11/1994 | Miyazaki et al. |
| 5,414,166 A | 5/1995 | Kim |
| 5,504,266 A | 4/1996 | Tirtowidjojo et al. |
| 5,684,219 A | 11/1997 | Boyce |
| 5,689,020 A | 11/1997 | Boyce |
| 5,811,605 A | 9/1998 | Tang |
| 5,895,825 A | 4/1999 | Elsheikh |
| 5,986,151 A | 11/1999 | Van Der Puy |
| 6,111,150 A | 8/2000 | Sakyu |
| 6,118,018 A | 9/2000 | Savidakis |
| 6,160,187 A | 12/2000 | Strickler |
| 6,187,976 B1 | 2/2001 | Van Der Puy |
| 6,229,057 B1 | 5/2001 | Jackson et al. |
| 6,235,951 B1 | 5/2001 | Sakyu et al. |
| 6,472,573 B1 | 10/2002 | Yamamoto |
| 6,518,467 B2 | 2/2003 | Tung et al. |
| 6,538,167 B1 | 3/2003 | Brown |
| 6,545,176 B1 | 4/2003 | Tsay |
| 6,551,469 B1 | 4/2003 | Nair |
| 6,610,177 B2 | 8/2003 | Tsay |
| 6,613,127 B1 | 9/2003 | Galloway |
| 6,683,216 B1 | 1/2004 | Zoeller |
| 6,825,383 B1 | 11/2004 | Dewkar |
| 6,924,403 B2 | 8/2005 | Barnes et al. |
| 6,958,135 B1 | 10/2005 | Filippi |
| 7,117,934 B2 | 10/2006 | Lomax |
| 7,189,884 B2 | 3/2007 | Mukhopadhyay |
| 7,226,567 B1 | 6/2007 | Olbert |
| 7,282,120 B2 | 10/2007 | Braun |
| 7,297,814 B2 | 11/2007 | Yada et al. |
| 7,345,209 B2 | 3/2008 | Mukhopadhyay |
| 7,371,904 B2 | 5/2008 | Ma et al. |
| 7,378,559 B2 | 5/2008 | Verwijs |
| 7,396,965 B2 | 7/2008 | Mukhopadhyay |
| 7,511,101 B2 | 3/2009 | Nguyen |
| 7,521,029 B2 | 4/2009 | Guetlhuber |
| 7,588,739 B2 | 9/2009 | Sugiyama |
| 7,659,434 B2 | 2/2010 | Mukhopadhyay |
| 7,674,939 B2 | 3/2010 | Mukhopadhyay |
| 7,687,670 B2 | 3/2010 | Nappa |
| 7,695,695 B2 | 4/2010 | Shin |
| 7,714,177 B2 | 5/2010 | Mukhopadhyay |
| 7,836,941 B2 | 11/2010 | Song |
| 7,880,040 B2 | 2/2011 | Mukhopadhyay |
| 7,951,982 B2 | 5/2011 | Mukhopadhyay |
| 8,058,486 B2 | 11/2011 | Merkel et al. |
| 8,058,490 B2 | 11/2011 | Strebelle |
| 8,071,825 B2 | 12/2011 | Johnson et al. |
| 8,071,826 B2 | 12/2011 | Van Der Puy |
| 8,076,521 B2 | 12/2011 | Elsheikh |
| 8,084,653 B2 | 12/2011 | Tung |
| 8,115,038 B2 | 2/2012 | Wilson |
| 8,123,398 B2 | 2/2012 | Teshima |
| 8,158,836 B2 | 4/2012 | Pigamo |
| 8,232,435 B2 | 7/2012 | Sievert |
| 8,258,353 B2 | 9/2012 | Tirtowidjojo |
| 8,258,355 B2 | 9/2012 | Merkel |
| 8,357,828 B2 | 1/2013 | Okamoto et al. |
| 8,367,867 B2 | 2/2013 | Zardi et al. |
| 8,383,867 B2 | 2/2013 | Mukhopadhyay |
| 8,395,000 B2 | 3/2013 | Mukhopadhyay |
| 8,398,882 B2 | 3/2013 | Rao |
| 8,487,146 B2 | 7/2013 | Wilson |
| 8,558,041 B2 | 10/2013 | Tirtowidjojo et al. |
| 8,581,011 B2 | 11/2013 | Tirtowidjojo et al. |
| 8,581,012 B2 | 11/2013 | Tirtowidjojo et al. |
| 8,614,361 B2 | 12/2013 | Suzuki |
| 8,614,363 B2 | 12/2013 | Wilson et al. |
| 8,907,148 B2 | 12/2014 | Tirtowidjojo et al. |
| 8,907,149 B2 * | 12/2014 | Tirtowidjojo ............ C07C 17/10 570/229 |
| 8,926,918 B2 | 1/2015 | Tirtowidjojo et al. |
| 8,933,280 B2 | 1/2015 | Tirtowidjojo et al. |
| 8,957,258 B2 | 2/2015 | Okamoto et al. |
| 9,056,808 B2 | 6/2015 | Tirtowidjojo et al. |
| 9,067,855 B2 | 6/2015 | Grandbois et al. |
| 2001/0018962 A1 | 9/2001 | Joshi et al. |
| 2002/0087039 A1 | 7/2002 | Tung et al. |
| 2002/0110711 A1 | 8/2002 | Boneberg et al. |
| 2005/0245774 A1 | 11/2005 | Mukhopadhyay et al. |
| 2006/0150445 A1 | 7/2006 | Redding |
| 2006/0258891 A1 | 11/2006 | Mukhopadhyay |
| 2006/0292046 A1 | 12/2006 | Fruchey |
| 2007/0197841 A1 | 8/2007 | Mukhopadhyay |
| 2007/0197842 A1 | 8/2007 | Tung |
| 2007/0265368 A1 | 11/2007 | Rao et al. |
| 2008/0021229 A1 | 1/2008 | Maughon |
| 2008/0073063 A1 | 3/2008 | Clavenna et al. |
| 2008/0118018 A1 | 5/2008 | Schrauwen |
| 2008/0207962 A1 | 8/2008 | Rao |
| 2009/0018377 A1 | 1/2009 | Boyce |
| 2009/0030249 A1 | 1/2009 | Merkel et al. |
| 2009/0088547 A1 | 4/2009 | Schamschurin et al. |
| 2009/0099396 A1 | 4/2009 | Mukhopadhyay |
| 2009/0117014 A1 | 5/2009 | Carpenter |
| 2009/0203945 A1 | 8/2009 | Mukhopadhyay |
| 2009/0253946 A1 | 10/2009 | Van Der Puy |
| 2009/0270568 A1 | 10/2009 | Strebelle et al. |
| 2010/0041864 A1 | 2/2010 | Kadowaki et al. |
| 2010/0185029 A1 | 7/2010 | Elsheikh |
| 2010/0263278 A1 | 10/2010 | Kowoll et al. |
| 2011/0087056 A1 | 4/2011 | Tirtowidjojo et al. |
| 2011/0155942 A1 | 6/2011 | Pigamo et al. |
| 2011/0172472 A1 | 7/2011 | Sakyu |
| 2011/0218369 A1 | 9/2011 | Elsheikh et al. |
| 2011/0251425 A1 | 10/2011 | Penzel |
| 2012/0065434 A1 | 3/2012 | Nose |
| 2014/0081055 A1 | 3/2014 | Tirtowidjojo |
| 2014/0163266 A1 | 6/2014 | Tirtowidjojo et al. |
| 2014/0179962 A1 | 6/2014 | Tirtowidjojo et al. |
| 2014/0323775 A1 | 10/2014 | Grandbois et al. |
| 2014/0323776 A1 | 10/2014 | Grandbois et al. |
| 2014/0336425 A1 | 11/2014 | Tirtowdjojo et al. |
| 2014/0336431 A1 | 11/2014 | Tirtowidjojo et al. |
| 2014/0371494 A1 | 12/2014 | Tirtowidjojo et al. |
| 2015/0045592 A1 | 2/2015 | Grandbois et al. |

(56) References Cited

U.S. PATENT DOCUMENTS

| | | |
|---|---|---|
| 2015/0057471 A1 | 2/2015 | Tirtowidjojo et al. |
| 2015/0217256 A1 | 8/2015 | Tirtowidjojo et al. |

FOREIGN PATENT DOCUMENTS

| | | |
|---|---|---|
| CN | 102001911 | 4/2011 |
| CN | 102249846 | 11/2011 |
| CN | 102351637 | 2/2012 |
| CN | 103562164 A | 2/2014 |
| DE | 857955 | 12/1952 |
| DE | 209184 | 4/1984 |
| DE | 235631 | 5/1986 |
| DE | 102005044501 | 3/2007 |
| DE | 102010022414 | 12/2011 |
| EP | 0131560 | 1/1985 |
| EP | 0164798 | 12/1985 |
| EP | 0453818 | 10/1991 |
| EP | 1018366 | 12/2000 |
| EP | 1097984 | 5/2001 |
| FR | 1546709 | 11/1968 |
| GB | 471186 | 8/1937 |
| GB | 471187 | 8/1937 |
| GB | 471188 | 8/1937 |
| GB | 857086 | 12/1960 |
| GB | 1134585 | 11/1968 |
| GB | 1381619 | 1/1975 |
| GB | 1548277 | 7/1979 |
| JP | 54079207 | 6/1979 |
| JP | S54-135712 | 10/1979 |
| JP | 08-119885 | 5/1996 |
| JP | 2001213820 | 8/2001 |
| JP | 2006272267 | 10/2006 |
| JP | 2007021396 | 2/2007 |
| JP | 2008063314 | 3/2008 |
| JP | 2007-535561 | 5/2008 |
| JP | 2009000592 | 1/2009 |
| JP | 2009046653 | 3/2009 |
| JP | 2001151708 | 6/2011 |
| JP | 2011144148 | 7/2011 |
| LU | 52247 | 12/1966 |
| SU | 899523 | 1/1982 |
| WO | 0138271 | 5/2001 |
| WO | 0138275 | 5/2001 |
| WO | 2005016509 | 2/2005 |
| WO | 2007079431 | 7/2007 |
| WO | 2007079435 | 7/2007 |
| WO | 2007096383 | 8/2007 |
| WO | 2008054781 | 5/2008 |
| WO | 2009015304 | 1/2009 |
| WO | 2009067571 | 5/2009 |
| WO | 2009087423 | 7/2009 |
| WO | 2011060211 | 5/2011 |
| WO | 2011065574 | 6/2011 |
| WO | 2012011844 | 1/2012 |
| WO | 2012081482 | 12/2012 |
| WO | 2012166393 | 12/2012 |
| WO | 2012166394 A1 | 12/2012 |
| WO | 2013082410 | 6/2013 |
| WO | 2014046970 | 3/2014 |
| WO | 2014046977 | 3/2014 |
| WO | 2014066083 | 5/2014 |
| WO | 2014100039 | 6/2014 |
| WO | 2014100066 | 6/2014 |
| WO | 2014134233 | 9/2014 |
| WO | 2014134377 | 9/2014 |
| WO | 2014164368 | 10/2014 |

OTHER PUBLICATIONS

Boualy, et al., "Kharasch Addition of Tetrachloromethane to Alkenes Catalyzed by Metal Acetylacetonates", "Kharasch Addition of Tetrachloromethane to Alkenes Catalyzed by Metal Acetylacetonates".

Chai, et al., "Study of Preparation of 1,1,1,3-tetrachloropropane", Zhejiang Chemical Industry, 2010, pp. 1-3, 41(5).

Evstigneev, et al., "Initiated Chlorination of Tetrachloropropane", Khim. Prom., 1984, pp. 393-394, 16(7).

Fields, et al., "Thermal Isomerization of 1,1-dichlorocyclopropanes", Chemical Communications, Jan. 1, 1967, p. 1081, 21.

Galitzenstein, et al., "The Dehydrochlorination of Propylene Dichloride", Journal of the Society of Chemical Industry, 1950, pp. 298-304, 69.

Gault, et al., "Chlorination of Chloroform", Comptes Rendus Des Seances De L'Academie des Sciences, 1924, pp. 467-469, 179.

Gerding, et al., "Raman Spectra of aliphatic chlorine compounds: chloroethenes an chloropropenes", Recueil Jan. 1, 1955, pp. 957-975, 74.

Hatch, et al., "Allylic Chlorides. XV. Preparation and Properties of the 1,2,3Trichloropropenes", JACS, Jan. 5, 1952, pp. 123-126, 74.

Hatch, et al., "Allylic Chlorides. XVIII. Preparation and Properties of 1,1,3-tricholoro-2-fluoro-1-propene and 1,1,2,3-tetrachloro-1-propene", JACS, Jul. 5, 1952, pp. 3328-3330, 74(13).

Herzfelder, "Substitution in the Aliphatic Series", Berichte Der Deutschen Chemischen Gesellschaft, May-Aug. 1893, pp. 1257-1261, 26(2).

Huaping, et al., "Procress in Synthesis of 1,1,1,3-tetrachloropropane", Guangzhou Chemicals, 2011, pp. 41-42, 39(5).

Ivanov, et al., "Metal phthalocyanine-Catalyzed Addition of polychlorine-Containing Organic Compounds to C=C Bonds", Russian Chemical Bulletin, International Edition, Nov. 2009, pp. 2393-2396, 58(11).

Kang, et al., "Kinetics of Synthesis of 1,1,1,3,3-pentachlorobutane Catalyzed by Fe—FeCl3", Chemical Research and Application, Jun. 2011, pp. 657-660, 23(6).

Kharasch, et al., "Chlorinations with Sulfuryl Chloride.I. The Peroxide-Catalyzed Chlorination of Hydrocarbons", JAGS, 1939, pp. 2142-2150, 61.

Khusnutdinov, et al., "CCl4 Attachment to Olefins Catalyzed by Chromium and Ruthenium Complexes. Impact of Water as a Nucleophilic Admixture", Oil Chemistry, 2009, pp. 349-356, vol. 4.

Kruper, et al., "Synthesis of alpha-Halocinnamate Esters via Solvolytic Rearrangement of Trichloroallyl Alcohols", J Org Chem, 1991, pp. 3323-3329, 56.

Leitch, "Organic Deuterium Compounds: V. The chlorination of propyne and propyne D-4", Canadian Journal of Chemistry, Apr. 1, 1953, pp. 385-386, 30(4).

Levanova, et al., "Cholorination of Chloroolefins C3-C4", Doklady Chemistry, vol. 386, No. 4, 2002, 496-498.

Levanova, et al., "Thermocatalytic Reactions of Bromochloropropanes", Russian Journal of Physical Chemistry, Jan. 1, 1983, pp. 1142-1146, 57.

McBee, et al., "Utilization of Polychloropropanes and Hexachloroethane", Industrial and Engineering Chemistry, Feb. 1, 1941, pp. 176-181, 33(2).

Michigan Technological Univ., "Free-Radical Chlorination with Sulfuryl Chloride", Nov. 15, 2001, 1-7.

Mouneyrat, "Effect of Chlorine on Propyl Chloride in the Presence of Anhydrous Aluminum Chloride", Bulletin de la Societe chimique de france, Societe francaise de chimie, Jan. 1, 1899, pp. 616-623, 21(3).

Munoz-Molina, et al., "An Efficient, Selective and Reducing Agent-Free Copper Catalyst for the Atom-Transfer Radical Addition of Halo Compounds to Activated Olefins", Inorg. Chem., 2010, pp. 643-645, 49.

Nair, et al., "Atom Transfer Radical Addition (ATRA) of Carbon Tetrachloride and Chlorinated Esters to Various Olefins Catalyzed by CP/Ru(PPh3)(PR3)Cl Complexes", Inorganica Chimica Acta, 2012, pp. 96-103, 380.

Nguyen, et al., "Condensation de chloroforme avec des olefins fluorees en milieu basique", Journal of Fluorine Chemistry, Dec. 1, 1991, pp. 241-248, 55(3).

Nikishin, et al., "Reactions of Methanol and Ethanol with Tetrachloroethylene", Izvestiya Akademii Nauk SSSR, Seriya Khimicheskaya, Dec. 1966, pp. 2188-2192, 12.

Ochi, et al., "Preparation of Chloropropenes by Photochemical Dehydrochlorination of 1,2-Dichloropropane", Chemical Abstracts, Jul. 17, 1989, p. 574, 111(3).

(56) References Cited

OTHER PUBLICATIONS

Pozdnev, et al., "Chlorination of chloroform and the conversion of methylene chloride manufacture still residues", Khim., Khim. Tekhnol., 1970, 70(4).

Rotshtein, et al., "Isomer Distribution on Chlorination of Chloropropanes", Z. Organicheskoi Khimii, 1966, pp. 1539-1542, 2(9).

Semenov, "Selectivity of Photochemical Chlorination of Chloromethane in the Liquid Phase", Prikladnei Khimii, 1985, pp. 840-845, 58(4).

Shelton, et al., "Addition of Halogens and Halogen Compounds to Allylic Chlorides. I. Addition of Hydrogen Halides", Journal of Organic Chemistry, 1958, pp. 1876-1880, 23.

Skell, et al., "Reactions of BrCl with alkyl radicals", Tetrahedron letters, 1986 pp. 5181-5184, 27(43).

Skell, et al., "Selectivities of pi and sigma succinimidyl radicals in substitution and addition reactions, Response to Walling, Wi-Taliawi and Zhao", JACS, Jul. 1, 1983, pp. 5125-5131, 105(15).

Stevens, "Some New Cyclopropanes with a Note on the Exterior Valence Angles of Cyclopropane", JACS, Vo. 68, No. 4, 1945, 620-622.

Tanuma, et al., "Partially Fluorinated Metal Oxide Catalysts for a Friedel-Crafts-type Reaction of Dichlorofluoromethane with Tetrafluoroethylene", Catal. Lett, 2010, pp. 77-82, 136.

Tobey, et al., "Pentachlorocyclopropane", Journal of the American Chemical Society, Jun. 1, 1996, pp. 2478-2481, 88 (11).

Urry, et al., "Free Radical Reactions of Diazomethane with Reactive Bromopolychloroalkane", JACS, May 5, 1964, pp. 1815-1819, 86(9.

Wang Chin-Hsien, "Elimination Reactions of polyhalopropanes under emulsion catalytic conditions to give Halopropenes", Synthesis, Jan. 1, 1982, pp. 494-496, 1982(6).

Zhao, et al., "Research Progress on Preparation Technology of 1,1,2,3-Tetrachloropropene", Zhejiang Chemical Industry, 2010, pp. 8-10, 41(6).

Zheng, et al., "Preparation of the low GWP alternative 1,3,3,3-tetrafluoropropene", Zhejiang Huagong, 2010, pp. 5-7, 41(3).

* cited by examiner

PROCESS FOR THE PRODUCTION OF CHLORINATED ALKANES

FIELD

The present invention relates to processes for the production of chlorinated alkanes, and in particular, to processes for the production of tri-, tetra- and pentachlorinated alkanes.

BACKGROUND

Hydrofluorocarbon (HFC) products are widely utilized in many applications, including refrigeration, air conditioning, foam expansion, and as propellants for aerosol products including medical aerosol devices, Although HFC's have proven to be more climate friendly than the chlorofluorocarbon and hydrochlorofluorocarbon products that they replaced, it has now been discovered that they exhibit an appreciable global warming potential (GWP).

The search for more acceptable alternatives to current fluorocarbon products has led to the emergence of hydrofluoroolefin (HFO) products. Relative to their predecessors, HFOs are expected to exert less impact on the atmosphere in the form of a lesser, or no, detrimental impact on the ozone layer and their lower GWP as compared to HFC's. Advantageously, HFO's also exhibit low flammability and low toxicity.

As the environmental, and thus, economic importance of HFO's has developed, so has the demand for precursors utilized in their production. Many desirable HFO compounds, e.g., such as 2,3,3,3-tetrafluoroprop-1-ene or 1,3,3,3-tetrafluoroprop-1-ene, may typically be produced utilizing feedstocks of chlorocarbons, and in particular, highly chlorinated alkanes, e.g., tri-, tetra- and pentachloroalkanes.

Unfortunately, these higher chlorides have proven difficult to manufacture using acceptable process conditions and in commercially acceptable regioselectivities and yields. For example, conventional processes for the production of trichloropropane (such as those disclosed in U.S. Pat. Nos. 2,119,484 and 4,051,182) provide unacceptable selectivity to the desired trichloropropane isomer, make use of suboptimal chlorinating agents, and/or require the use of expensive catalyst systems and/or initiators. Suboptimal selectivity to the trichloropropane often unfortunately leads to an even further reduction in selectivity to the desired higher chlorinated alkanes, e.g., tetra- and pentachlorinated alkanes.

It would thus be desirable to provide improved processes for the production of chlorocarbon precursors useful as feedstocks in the synthesis of refrigerants and other commercial products. More particularly, such processes would provide an improvement over the current state of the art if they provided a higher regioselectivity relative to conventional methods, made use of optimal chlorinating agents and/or made use of less expensive catalyst systems and/or initiators.

BRIEF DESCRIPTION

The present invention provides efficient processes for the production of chlorinated alkanes. More particularly, the processes make use of a trichlorinated alkane to produce tetra- and pentachloroalkanes with high selectivity. In some embodiments, the processes advantageously make use of 1,1,2-trichloropropane, which, in some embodiments, may be produced in situ via the ionic chlorination of 1,2-dichloropropane. The desired starting material is initially dehydrochlorinated and as a result, selectivity of the process to, e.g., 1,1,1,2,2-pentachloropropane, is enhanced over conventional processes that utilize only chlorination steps.

In one aspect, the present invention provides a process for the production of tetra- and/or pentachlorinated alkanes from one or more trichlorinated alkanes. The trichlorinated alkane comprises from 3-6 carbon atoms, or from 3-5 carbon atoms, or from 3-4 carbon atoms, or 3 carbon atoms and desirably comprises vicinal chlorine atoms. In some embodiments, the trichlorinated alkane comprises 1,1,2-trichloropropane.

The process comprises first dehydrochlorinating the one or more trichlorinated alkanes, rather than subjecting the same to a first chlorination step. This initial dehydrochlorination is desirably conducted in the presence of caustic, rather than catalytically. The trichlorinated alkane may advantageously be produced in situ by the ionic chlorination of a dichlorinated alkane, e.g., 1,2-dichloropropane. The product stream of the dehydrochlorination of the trichlorinated alkane is subjected to sequential chlorination and/or further dehydrochlorination steps. In some embodiments, all steps after the initial dehydrochlorination may be chlorination steps, or the process may comprise a combination, such as an alternating combination, of chlorination and dehydrochlorination steps.

Any or all of the chlorination steps within the process may be conducted in presence of an ionic chlorination catalyst. Suitable ionic chlorination catalysts include Lewis acids, such as, aluminum chloride ($AlCl_3$), iodine ($I_2$), ferric chloride ($FeCl_3$), sulphur, antimony pentachloride, boron trichloride, one or more lanthanum halides, one or more metal triflates, or combinations of these. In some embodiments, any ionic chlorinations may desirably be carried out in the presence of aluminum chloride. Chlorine, sulfuryl chloride ($SO_2Cl_2$) or combinations of these, may be used as chlorinating agents in any, some or all chlorination steps. In sonic embodiments, one or more chlorinations may be conducted in the presence of a solvent, such as, e.g., methylene chloride, carbon tetrachloride, and/or 1,1,2,3-tetrachloropropane.

The first and/or any further dehydrochlorinations used in the process are desirably conducted in the liquid phase, and may be conducted in the presence of one or more chemical bases, caustic, potassium hydroxide, calcium hydroxide or a combination of these. Phase transfer catalysts may also be used and suitable examples of these include quaternary ammonium and quaternary phosphonium salts.

The liquid phase dehydrochlorination of the trichloroalkane is highly selective and as a result, the number of separation or purification steps used in the process can be reduced as compared to conventional processes for the production of chlorinated alkanes that chlorinate this intermediate. In some embodiments, no purification steps may be necessary between dehydrochlorination and chlorination steps.

Any chlorinated alkane may be produced by the process, but due to its importance as a feedstock in other processes for the production of refrigerants, the production of 1,1,1,2,2-pentachloropropane is contemplated in some embodiments.

DETAILED DESCRIPTION

Figure 1:
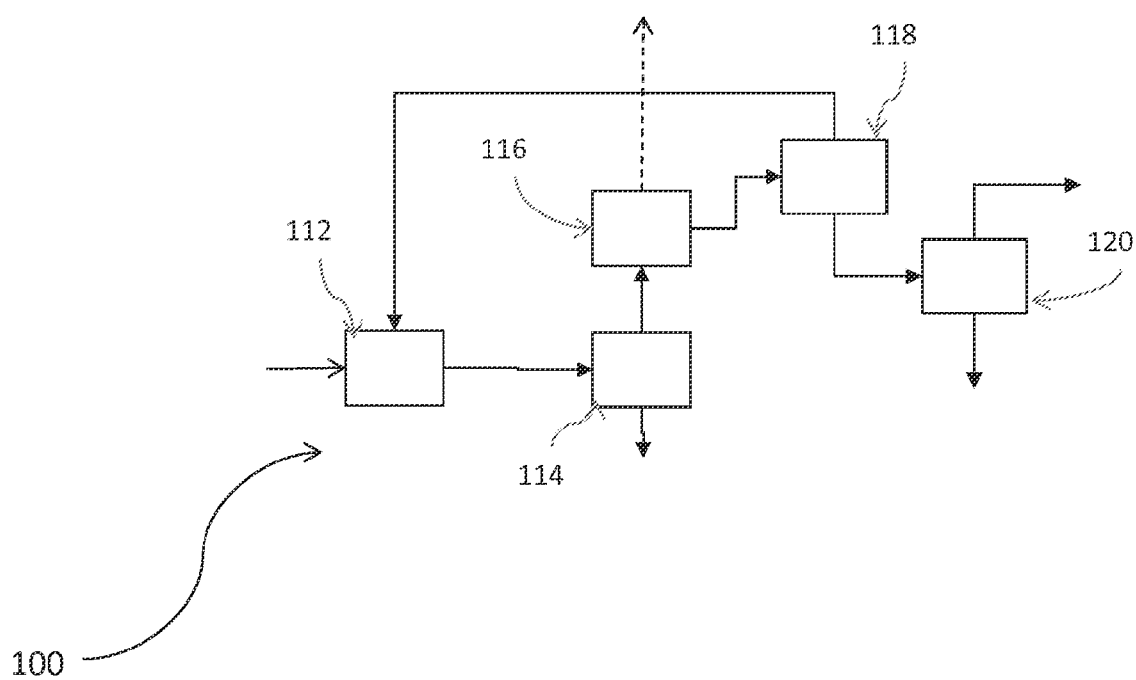
FIG. 1 shows a schematic representation of a process according to one embodiment.

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

if ranges are disclosed, the endpoints of all ranges directed to the same component or property are inclusive and independently combinable (e.g., ranges of "up to 25 wt. %, or, more specifically, 5 wt. % to 20 wt. %," is inclusive of the endpoints and all intermediate values of the ranges of "5 wt % to 25 wt. %," etc.). As used herein, percent (%) conversion is meant to indicate change in molar or mass flow of reactant in a reactor in ratio to the incoming flow, while percent (%) selectivity means the change in molar flow rate of product in a reactor in ratio to the change of molar flow rate of a reactant.

Reference throughout the specification to "one embodiment" or "an embodiment" means that a particular feature, structure, or characteristic described in connection with an embodiment is included in at least one embodiment. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

The present invention provides efficient processes for the production of chlorinated alkanes. The present processes comprise reacting one or more trichlorinated alkanes to provide tetra- and/or pentachlorinated alkanes, with high regioselectivity. More particularly, the present processes first dehydrochlorinate the trichloroalkane, rather than first chlorinating this material, as may have been done in conventional processes. Selectivity to the corresponding 1,1-dichloroalkene is enhanced, and further reaction steps lead to, e.g., 1,1,1,2,2-pentachloropropane with enhanced selectivity as well.

Any trichlorinated alkane having from 3-6 carbon atoms, or from 3-5 carbon atoms, or from 3-4 carbon atoms, or 3 atoms, can be utilized as a starting material in the process. The trichlorinated alkane desirably comprises vicinal chlorine atoms, i.e., chlorine atoms present on adjacent carbon atoms. The use of vicinal trichlorinated alkanes with two chlorine atoms in the first carbon is thought to contribute to the regioselectivity provided by the process, and such trichlorinated alkanes are preferred in some embodiments. For example, in those embodiments wherein the starting material comprises the vicinal trichloropropane 1,1,2-trichloropropane, regioselectivity to 1,1,1,2-tetrachloropropane and/or 1,1,1,2,2-pentachloropropane can be seen.

In some embodiments, the 1,1,2-trichloropropane may be produced in situ, e.g., via the ionic chlorination of 1,2-dichloropropane. The use of 1,2-dichloropropane as a feedstock for the production of 1,1,2-trichloropropane used in the process is advantageous, since it may be available at low cost due to its production as a by-product in many chlorohydrin processes.

The tetra-, and/or pentachlorinated alkane produced by the process will depend upon the trichlorinated alkane used as a starting material. And so, the processes can be used to produce alkanes comprising from 3-6 carbon atoms, or from 3-5 carbon atoms, or from 3-4 carbon atoms. In some embodiments, and due to the commercial significance of tetra- and pentachlorinated propanes and butanes, the use of one or more di- and/or trichlorinated propanes and butanes as starting materials may be preferred. In some embodiments, 1,1,2-trichloropropane is utilized as a starting material to produce 1,1,1,2-tetrachloropropane and/or 1,1,1,2,2-pentachloropropane at high selectivity.

One or more of the dehydrochlorination steps of the present process may be conducted in the presence of a liquid caustic. Although vapor phase dehydrochlorinations could be used, liquid phase dehydrochlorination reactions provide higher selectivity to the desired intermediates. Liquid phase dehydrochlorinations also provide the opportunity for cost savings since evaporation of reactants is not required. The lower reaction temperatures used in liquid phase reactions may also result in slower fouling rates than those observed in connection with the higher temperature gas phase reactions, and so reactor lifetimes may also be optimized when at least one liquid phase dehydrochlorination is utilized.

Many chemical bases are known in the art to he useful for liquid dehydrochlorinations, and any of these can be used. For example, suitable bases include, but are not limited to, alkali metal hydroxides, such as sodium hydroxide, potassium hydroxide, calcium hydroxide; alkali metal carbonates such as sodium carbonate; lithium, rubidium, and cesium or combinations of these. Phase transfer catalysts such as quaternary ammonium and quaternary phosphonium salts (e.g. benzytrimethylammonium chloride or hexadecyltributylphosphonium bromide) can also be added to improve the dehydrohalogenation reaction rate with these chemical bases.

The product from the dehydrochlorination of the trichlorinated alkane is subsequently subjected to a series of chlorination anchor dehydrochlorination steps. All remaining steps of the process may be chlorination steps, or less than all, or only one. Desirably, the chlorination steps used in the process are conducted in the presence of ionic chlorination catalysts, which further enhance the specificity of the process.

The specificity of the process is further enhanced by the use of a Lewis acid as an ionic chlorination catalyst. The use of ionic chlorination catalysts in the present process is particularly advantageous since they can promote dehydrochlorination and catalyze chlorination reactions within the same reactor. That is, ionic chlorination catalysts remove a chlorine and hydrogen from adjacent carbon atoms, the adjacent carbon atoms form a double bond, and HCl is released. A chlorine molecule is then added back, replacing the double bond, to provide a more highly chlorinated alkane.

Ionic chlorination catalysts are well known to those of ordinary skill in the art and any of these may be used in the present process. Exemplary ionic chlorination catalysts include, but are not limited to, aluminum chloride, ferric chloride ($FeCl_3$) and other iron containing compounds, iodine, sulfur, antimony pentachloride ($SbCl_5$), boron trichloride ($BCl_3$), lanthanum halides, metal triflates, and combinations thereof. Of these, aluminum chloride and ferric chloride are Lewis acids, and so, their use in the process may be preferred in some embodiments.

Any or all of the catalysts utilized in the process can be provided either in bulk or in connection with a substrate, such as activated carbon, graphite, silica, alumina, zeolites, fluorinated graphite and fluorinated alumina. Whatever the desired catalyst (if any), or format thereof, those of ordinary skill in the art are well aware of methods of determining the appropriate format and method of introduction thereof. For example, many catalysts are typically introduced into the reactor zone as a separate feed, or in solution with other reactants.

The amount of any ionic chlorination and/or dehydrochlorination catalyst utilized will depend upon the particular catalyst chosen as well as the other reaction conditions. Generally speaking, in those embodiments of the invention wherein the utilization of a catalyst is desired, enough of the catalyst should be utilized to provide some improvement to reaction process conditions (e.g., a reduction in required temperature) or realized products, but yet not he more than will provide any additional benefit, if only for reasons of economic practicality.

For purposes of illustration only then, it is expected, that useful concentrations of the ionic chlorination catalyst will range from 0.001% to 20% by weight, or from 0.01% to 10%, or from 0.1% to 5 wt. %, inclusive of all subranges therebetween. If a dehydrochlorination catalyst is utilized for one or more dehydrochlorination steps, useful concentrations may range from 0.01 wt. % to 5 wt. %, or from 0.05 wt. % to 2 wt. % at temperatures of from 70° C. to 200° C. If a phase transfer catalyst is utilized, useful concentrations may typically be less than 0.1 wt %, or less than 1000ppm. Relative concentrations of each catalyst are given relative to the feed of reactant, including any recycled reactants and/or intermediates to the reaction vessel, if a chemical base is utilized for one or more dehydrochlorinations, useful concentrations of these will range from 0.01 to 20 grmole/L, or from 0.1 grmole/L to 15 grmole/L, or from 1 grmole/L to 10 grmole/L, inclusive of all subranges therebetween.

The chlorination steps of the process may be carried out using any chlorination agent, and several of these are known in the art. For example, suitable chlorination agents include, but are not limited to chlorine, and/or sulfuryl chloride ($SO_2Cl_2$). Combinations of chlorinating agents may also be used. Either or both $Cl_2$ and sulfuryl chloride may be particularly effective when aided by the use of the aforementioned ionic chlorination catalysts. In some embodiments, one or more chlorination steps may be conducted in the presence of a solvent, such as, e.g., methylene chloride, carbon tetrachloride, and 1,1,2,3-tetrachloropropane, or combinations of these.

The reaction conditions under which the process is carried out in liquid phase and thus are advantageously low intensity. That is, low temperatures, e.g., of less than 100° C., or less than 90° C., or less than 80° C. or less than 70° C., or less than 60° C., or less than 50° C., or even as low as 40° C. may be utilized and the desired selectivities to the tri-, tetra-, and/or pentachloroalkanes yet be realized. In some embodiments, temperatures of from 40° C. to 70° C. or 55° C. to 65° C., may be utilized. Similarly, ambient pressure is suitable for carrying out the process, or pressures within 250, or 200, or 150, or 100, or 50, or 40, or 30, or 20, or even 10 psi, of ambient are suitable. Reactor occupancy may also be minimized with the desired selectivities yet seen for example, reactor occupancy times of less than 20 hours, or less than 15 hours, or less than 10 hours, or less than 5 hours, or less than 4, 3, 2, or even 1 hour, are possible. The reactor may be any suitable liquid phase reactor, such as a batch, semi-batch or continuous stirred tank autoclave reactor with an internal cooling coil. A shell and multitube exchanger followed by vapor liquid disengagement tank or vessel can also be used.

In additional embodiment, one or more reaction conditions of the process may be optimized, in order to provide even further advantages, i.e., improvements in selectivity, conversion or production of reaction by-products. In certain embodiments, multiple reaction conditions are optimized and even further improvements in selectivity, conversion and production of reaction by-products produced can be seen.

Reaction conditions of the process that may be optimized include any reaction condition conveniently adjusted, e.g., that may be adjusted via utilization of equipment and/or materials already present in the manufacturing footprint, or that may be obtained at low resource cost. Examples of such conditions may include, but are not limited to, adjustments to temperature, pressure, flow rates, molar ratios of reactants, etc.

That being said, the particular conditions employed at each step described herein are not critical, and are readily determined by those of ordinary skill in the art. What is important is that a feedstream comprising a trichloroalkane having from 3-6 carbon atoms and further comprising at least two vicinal chlorine atoms is first subjected to a dehydrochlorination step, rather than a chlorination step. Those of ordinary skill in the art will readily be able to determine suitable equipment for each step, as well as the particular conditions at which the chlorination, dehydrochlorination, separation, drying, and isomerization steps may be conducted.

In one exemplary process, 1,1,2-trichloropropane is dehydrochlorinated, using caustic, to provide 1,1-dichloropropene. The 1,1,2-trichloropropane may be provided in situ, e.g., via the reaction of 1,2-dichloropropane (PDC) with sulfuryl chloride in the presence of aluminum chloride at a temperature of from 55° C. to 65° C., ambient pressure and a reactor occupancy of less than one hour.

The 1,1-dichloropropene is then chlorinated to provide 1,1,1,2-tetrachloropropane, which is then dehydrochlorinated using caustic or catalytically, to provide 1,1,2-trichloropropene. The 1,1,2-trichloropropene is then chlorinated to provide 1,1,1,2,2-pentachloropropane. In other embodiments, the 1,1,1,2-tetrachloropropane may be chlorinated, and in such embodiments, all steps after the initial dehydrochlorination of the 1,1,2-trichloropropane would be chlorination steps.

A schematic illustration of one embodiment of such a process is shown in FIG. 1. As shown in FIG. 1, process 100 incorporates dehydrochlorination reactor 112, drying unit 114, chlorination reactor 116, and separation units 118 and 120.

In operation of process 100, 1,1,2-trichloropropane and recycled 1,1,1,2-tetrachloropropane are fed to dehydrochlorination reactor 112, wherein they are dehydrochlorinated using caustic to produce 1,1-dichloropropene and 1,1,2-trichlosopropene, respectively. The product stream from dehydrochlorination reactor 112 is then dried in drying unit 114 and fed to chlorination reactor 116.

The dried product stream from dehydrochlorination reactor, comprising 1,1-dichloropropene and 1,1,2-trichloropropene, is chlorinated in chlorination reactor 116 to provide 1,1,1,2-tetrachloropropane and 1,1,1,2,2-pentachloropropane respectively. Any excess $Cl_2$ and any HCl byproduct may he vented off an overhead stream and provided to a purification unit (not shown) for recovery of the HCl and $Cl_2$. Any recovered $Cl_2$ may be recycled to chlorination reactor 116, if desired.

The product stream from chlorination reactor 116, comprising 1,1,2-tetrachloropropane and 1,1,1,2,2-pentachloropropane, is fed to separation unit 118. Separation unit 118 is operated at conditions effective to provide unreacted di- and trichloropropenes and 1,1,1,2-tetrachloropropane as an overhead stream, which may be recycled to dehydrochlorination reactor 112. if desired. The bottom stream of separation unit, comprising 1,1,1,2,2-pentachloropropane, is fed to separation unit 120 which is operated at conditions effective to provide 1,1,1,2,2-pentachloropropane as an overhead stream. The 1,1,1,2,2-pentachloropropane may optionally be recovered with a solvent, e.g., such as 1,1,2,3-tetrachloropropane, other pentachloropropane isomers or the hexachloropropane byproduct. Further purification methods, such as crystallization, may be used to purify the 1,1,1,2,2-pentachloropropane, if desired.

Figure 2:
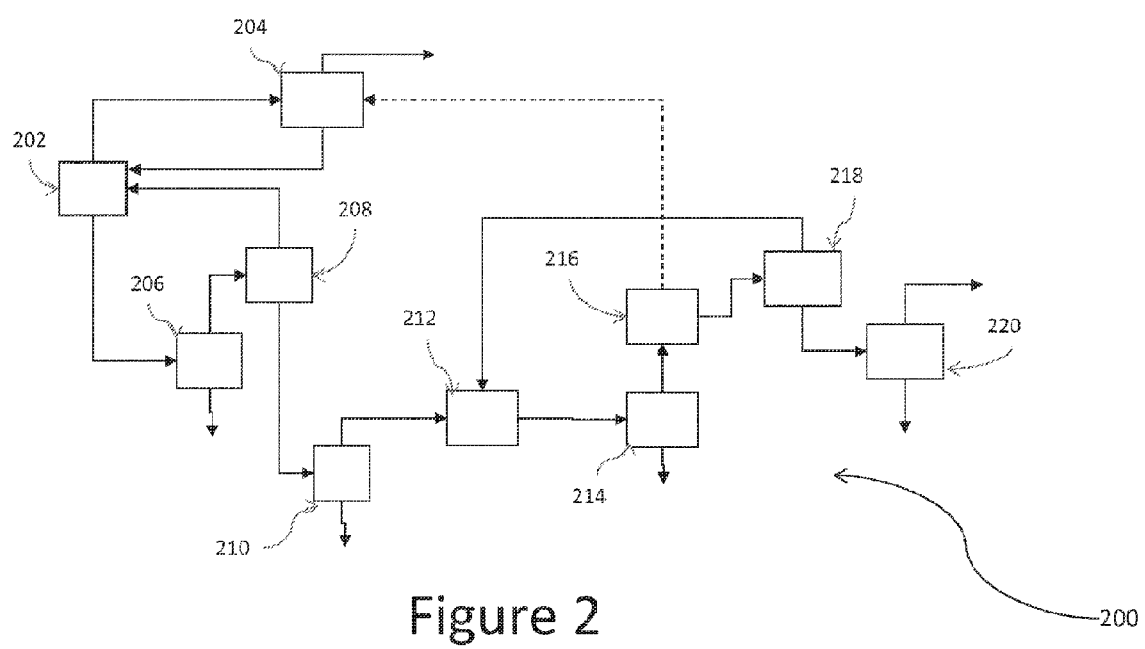
FIG. 2 shows a schematic representation of a process according to another embodiment.

A schematic illustration of another embodiment of the process is shown in FIG. 2. More particularly, in process 200, the 1,1,2-trichloropropane is provided in situ, via the chlorination of 1,2-dichloropropane. Process 200 thus includes chlorination reactor 202, HCl recovery unit 204, quench/drying unit 206, and separation units 208 and 210, in addition to the components used in process 100, identified with similar reference numerals incremented by 100.

In operation, 1,2-dichloropropane is fed to chlorination reactor 202 and chlorinated in the presence of a catalytic aluminum chloride to produce 1,1,2-trichloropropane and anhydrous HCl as byproduct. The HCl and excess chlorine is fed to HCl purification unit 204 where anhydrous HCl is purified and taken as the overhead stream. The bottom stream comprising $Cl_2$ is then recycled back to reactor 202. The bottom product stream of chlorination reactor 202, comprising 1,1,2-trichloropropane, is quenched to remove aluminum chloride in the aqueous phase. The organic product is dried in drying; unit 206 and the dried stream provided to separation unit 208.

Separation unit 208 is operated at conditions effective to provide 1,2-dichloropropane as an overhead stream and a bottom stream comprising 1,1,2-trichloropropane and 1,2,3-trichloropropane. The overhead stream from separation unit may be recycled to chlorination reactor 202, while the bottoms stream is provided to separation unit 210. Separation unit is operated at conditions effective to provide 1,1,2-trichloropropane as an overhead stream and 1,2,3-trichloropropane as a bottoms stream. The bottoms stream may be appropriately disposed of, while the overhead stream, consisting of substantially pure 1,1,2-trichloropropane is provided to dehydrochlorination reactor 212. The rest of process 200 proceeds as described in FIG. 1.

Figure 3:
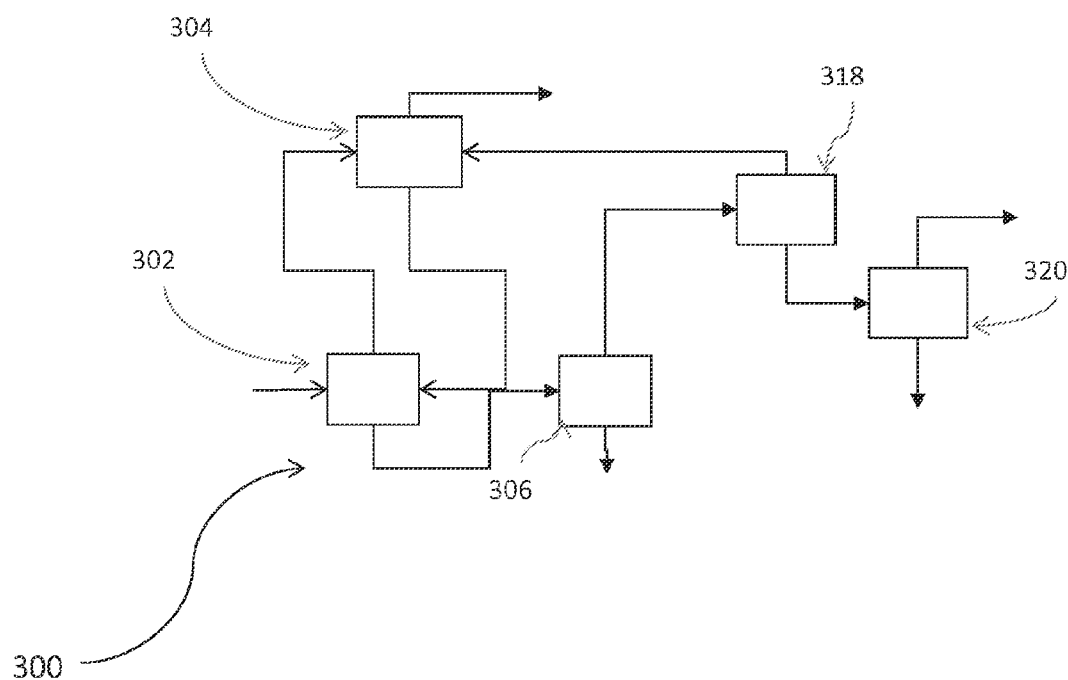
FIG. 3 shows a schematic representation of a process according to another embodiment.

A schematic illustration of another embodiment of the process is shown in FIG. 3. More particularly, process 300 makes use of 1,1-dichloropropene as a starting material. Process 300 thus includes chlorination reactor 302, HCl recovery unit 304, quench/drying unit 306, and separation units 318 and 320.

In operation of process 310, 1,1-dichloropropene is fed to chlorination reactor 302 and chlorinated in the presence of a catalytic amount of aluminum chloride to produce 1,1,1,2,2-pentachloropropane, 1,1,1,2-tetrachloropropane intermediate, and anhydrous HCl as a byproduct. The HCl and excess chlorine is fed to HCl purification unit 304 where anhydrous HCl is purified and taken as the overhead stream. The bottom stream comprising $Cl_2$ is then recycled back to reactor 302. The bottom product stream of chlorination reactor 302, comprising 1,1,1,2,2-pentachloropropane, 1,1,1,2-tetrachloropropane, and heavies is quenched to remove aluminum chloride in the aqueous phase. The organic product is dried in drying unit 306 and the dried stream provided to separation unit 318.

Separation unit 318 is operated at conditions effective to provide unreacted 1,1-dichloropropene and 1,1,1,2-tetrachloropropane as an overhead stream and a bottom stream comprising 1,1,1,2,2-pentachloropropane and heavies. The overhead stream from separation unit 318 may be recycled to chlorination reactor 302 via the HCl recovery unit 304, while the bottoms stream is provided to separation unit 320. Separation unit 320 is operated at conditions effective to provide 1,1,1,2,2-pentachloropropane as an overhead stream and heavies, i.e. 1,1,1,2,2,3-hexachloropropane, as a bottom stream, Some embodiments of the invention will now be described in detail in the following examples.

EXAMPLE 1

Preparation of 1,1-dichlororene from 1,1,2-trichloropropane

A round-bottom flask is charged with 1,1,2-trichloropropane (40.7 g) and benzyl trimethylammonium chloride (1.97 g) and heated to 70° C. and then charged with aqueous caustic solution (5,0N, 60 mL). After 4 hours, the solution is cooled to ambient temperature. The phases are separated and the aqueous phase is extracted with an equal volume of methylene chloride. The organic phases are combined and dried over magnesium sulfate. The dried crude solution contains 1,1,-dichloropropene as determined by GC and NMR spectroscopic analysis (24.5 g, 80.6% yield) dissolved in methylene chloride. $^1$H NMR ($CDCl_3$, 500 MHz): ppm=5.90 (q, 1H), 1,76 (d, 3H).

EXAMPLE 2

Preparation of 1,1,1,2-Tetrachloropropane from 1,1-dichloropropene

A 100 mL Parr vessel is charged with the dried crude product mixture from Example 1 containing 1,1-dichloropropene (24.5 g) and sealed. The reactor is pressurized to 125 psig and heated to 50° C. while $Cl_2$ (30% v/v in $N_2$, 200 sccm) is fed to the reactor. The chlorine flow is halted after 90 minutes and the reactor is returned to ambient temperature and pressure. The crude reaction mixture is analyzed by GC to indicate that the mixture is composed of 84.0% 1,1,1,2-tetrachloropropane, 6.6% 1,1,1,2,2-pentachloropropane, 6.0% 1,1-dichloropropene, and a balance of unidentified low-level byproducts. The crude reaction mixture is neutralized with aqueous sodium bicarbonate to remove residual dissolved chlorine and dried over magnesium sulfate. The crude material is purified by vacuum distillation (24 torr, 59° C.) to give 1,1,1,2-tetrachloropropane (19.7 g, 48.9% yield). $^1$H NMR ($CDCl_3$, 500 MHz): ppm=4.60 (q, 1H), 1.85 (d, 3H). $^{13}$C NMR ($CDCl_2$, 500 MHz): ppm=101.67, 68.46, 21.46. GC-MS: M$^+$=145, 109, 83, 75, 63.

EXAMPLE 3

Preparation of 1,1,2-trichloropropene from 1,1,1,2-tetrachloropropane

A round-bottom flask is charged with 1,1,1,2-tetrachloropropane (18.0 g) and benzyl trimethylammonium chloride (1.84 g) and heated to 70° C. and then charged with aqueous caustic solution (5.0N, 20 mL). The solution is stirred for 24 hours and then cooled to ambient temperature. The phases are separated and the aqueous phase is extracted with an equal volume of methylene chloride. The organic phases are combined and dried over magnesium sulfate and filtered. The dried crude liquid is concentrated under reduced pressure and then analyzed by $^1$H NMR and GC and determined to contain 1,1,2-trichloropropene as the major product. $^1$H NMR (CDCl$_3$, 500 MHz): ppm 2.28 (s, 3H). This product mixture is used without further purification in the subsequent Example 4.

EXAMPLE 4

Preparation of 1,1,2,2-pentachloropropane from 1,1,2-trichloropropene

This crude product mixture from Example 3 is dried with molecular sieves and then charged to a 100 mL Parr vessel and sealed. The reactor is pressurized to 125 psig with Cl$^2$ (30% v/v in N$_2$, 200 sccm) and heated to 50° C. while Cl$_2$ (30% v/v in N$_2$, 200 sccm) is fed to the reactor. The chlorine flow is halted after 90 minutes and the reactor is returned to ambient temperature and pressure. The crude reaction mixture is neutralized with aqueous sodium bicarbonate and then dried over magnesium sulfate. The crude material is purified by evaporation of the solvent to give 1,1,1,2,2-pentachloropropane (3.8 g, 21.5% yield) as a white solid. $^1$H NMR (CDCl$_3$, 500 MHz): ppm=2.51 (s). $^{13}$C NMR (CDCl$_3$, 500 MHz): ppm=104.81, 95.02, 33.11. GC-MS: M$^+$=181, 143, 97. Although selectivity in this particular example is high, the yield is believed low due to the volatility of the product, which may be ameliorated with handling techniques specific to accommodating this volatility.

EXAMPLE 5

Preparation of 1,1,1,2,2-pentachloropropane from 1,1-dichloropropene

A 300 mL Parr vessel is charged with the dried crude product mixture from Example 1 containing 1,1-dichloropropene (3.4 g), methylene chloride (50 mL), and aluminum chloride (0.1 g) and sealed. The reactor is pressurized to 125 psig with Cl$_2$ (30% v/v in N$_2$, 200 sccm) and heated to 70° C., while Cl$_2$ (30% v/v in N$_2$, 50 sccm) is fed to the reactor. The reaction mixture was analyzed by GC after 20 minutes and found to be comprised of 68.2% 1,1,1,2,2-pentachloropropane and 24.2% 1,1,1,2,2,3-hexachloropropane with a balance of low-level chlorinated propanes.

EXAMPLE 6

Preparation of 1,1,2,2-pentachloropropane from 1,1,1,2-tetrachloropropane

A 300 mL Parr vessel is charged with 1,1,1,2-tetrachloropropane (2.94 g), methylene chloride (50 mL) ferric chloride (0.13 g) and sealed. The reactor is pressurized to 125 psig with Cl$_2$ (30% v/v in N$_2$, 200 sccm) and heated to 70° C. while Cl$_2$ (30% v/v in N$_2$, 50 sccm is fed to the reactor. The reaction mixture was analyzed by GC after 60 minutes to be comprised of 77.9% unreacted 1,1,1,2-tetrachloropropane starting material, 13.4% 1,1,1,2,2-pentachloropropane, and 4.3% 1 1,1,2,2,3-hexachloropropane with a balance of low level chlorinated propanes.

The invention claimed is:

1. A process for the production of 1,1,1,2,2-pentachloropropane from 1,1,2-trichloropropane, the process comprising dehydrochlorinating the trichlorinated alkane and subjecting the product stream of the dehydrochlorination to sequential chlorination and/or further dehydrochlorination steps.

2. The process of claim 1, wherein the trichlorinated alkane is dehydrochlorinated in the presence of caustic.

3. The process of claim 1, wherein the 1,1,2-trichloropropane is produced in situ by the ionic chlorination of a dichlorinated alkane.

4. The process of claim 3, wherein the dichlorinated alkane comprises 1,2-dichloropropane.

5. The process of claim 1, wherein chlorination steps and dehydrochlorination steps are alternated after the dehydrochlorination of the trichloroalkane.

6. The process of claim 5, wherein the chlorination steps are conducted in a solvent.

7. The process of claim 6, wherein the solvent comprises methylene chloride, carbon tetrachloride, and/or 1,1,2,3-tetrachloropropane.

8. The process of claim 5, wherein the chlorination steps are conducted in the presence of an ionic chlorination catalyst comprising AlCl$_3$, I$_2$, FeCl$_3$, sulphur, antimony pentachloride, boron trichloride, one or more lanthanum halides, one or more metal triflates, or combinations of these.

9. The process of claim 8, wherein the ionic chlorination catalyst comprises AlCl$_3$.

10. The process of claim 1, wherein the first and/or further dehydrochlorination(s) is/are conducted in the liquid phase using caustic, potassium hydroxide, calcium hydroxide or a combination of these.

11. The process of claim 10, wherein the first and/or further dehydrochlorination(s) is/are conducted in the presence of one or more phase transfer catalysts comprising benzyltrimethylammonium chloride.

* * * * *